US00PP24779P3

(12) United States Plant Patent
Gargiulo

(10) Patent No.: US PP24,779 P3
(45) Date of Patent: Aug. 19, 2014

(54) GRAPEVINE PLANT NAMED 'CAR98-710'

(50) Latin Name: *Vitis vinifera*
Varietal Denomination: CAR98-710

(71) Applicant: M. Caratan, Inc., Delano, CA (US)

(72) Inventor: Angel A. Gargiulo, Mendoza (AR)

(73) Assignee: M. Caratan, Inc., Delano, CA (US)

( * ) Notice: Subject to any disclaimer, the term of this patent is extended or adjusted under 35 U.S.C. 154(b) by 22 days.

(21) Appl. No.: 13/694,972

(22) Filed: Jan. 23, 2013

(65) Prior Publication Data

US 2014/0208468 P1 Jul. 24, 2014

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Anne Grunberg
(74) *Attorney, Agent, or Firm* — Jondle Plant Sciences Division of Swanson & Bratschun, L.L.C.

(57) ABSTRACT

A new and distinct variety of grapevine plant named 'CAR98-710' particularly distinguished by black colored, seedless berries, medium to large berries and clusters, and excellent integrity of clusters and berries through October, is disclosed.

5 Drawing Sheets

Genus and species: *Vitis vinifera.*
Variety denomination: 'CAR98-710'.

BACKGROUND OF THE NEW PLANT

The present invention comprises a new and distinct variety of grapevine botanically known as *Vitis vinifera* and hereinafter referred to by the variety name 'CAR98-710'. The new variety originated from a cross conducted in May 1998 in Delano, Calif. between the female grapevine plant named 'Black Globe' (U.S. Plant Pat. No. 17,875) and the male grapevine plant named '552' (U.S. Plant Pat. No. 9,916). A single plant was selected for further evaluation and asexual propagation.

The new variety was first propagated in December 2005 in Delano, Calif. by vegetative cuttings and has been asexually reproduced repeatedly by vegetative cuttings for 3 generations. 'CAR98-710' has been found to retain its distinctive characteristics through successive asexual propagations.

Plant Breeder's Rights for this variety have not been applied for. 'CAR98-710' has not been made publicly available anywhere in the world more than one year prior to filing of this application.

SUMMARY OF THE INVENTION

The following are the most outstanding and distinguishing characteristics of this new variety when grown under normal horticultural practices in Delano, Calif.

1. Black colored, seedless berries;
2. Medium to large berries and clusters; and
3. Excellent integrity of clusters and berries through October.

DESCRIPTION OF THE PHOTOGRAPHS

This new grapevine plant is illustrated by the accompanying photographs which show clusters of fruit, leaves, canes, tendrils and berries. The colors shown are as true as can be reasonably obtained by conventional photographic procedures. The photographs are taken from a mature plant about 7 years old, grown in a field in Delano, Calif.

Figure 1:
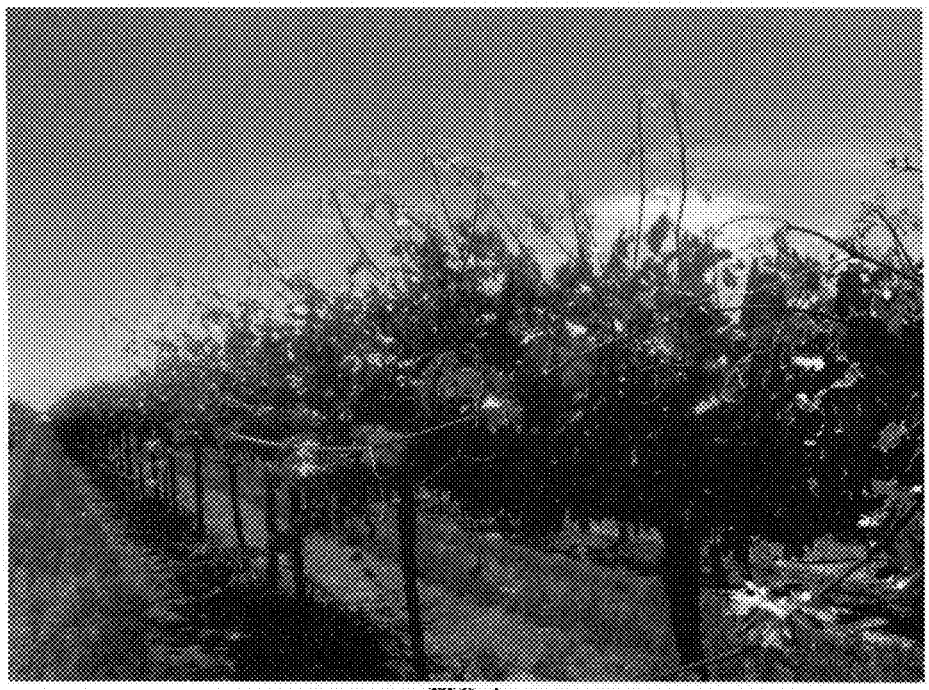
Figure 2:
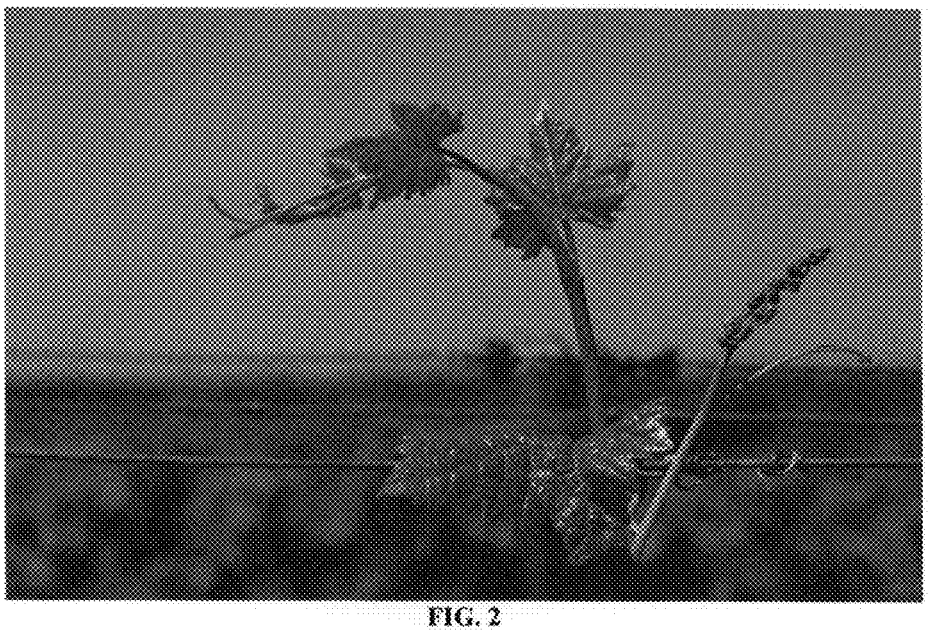
Figure 3:
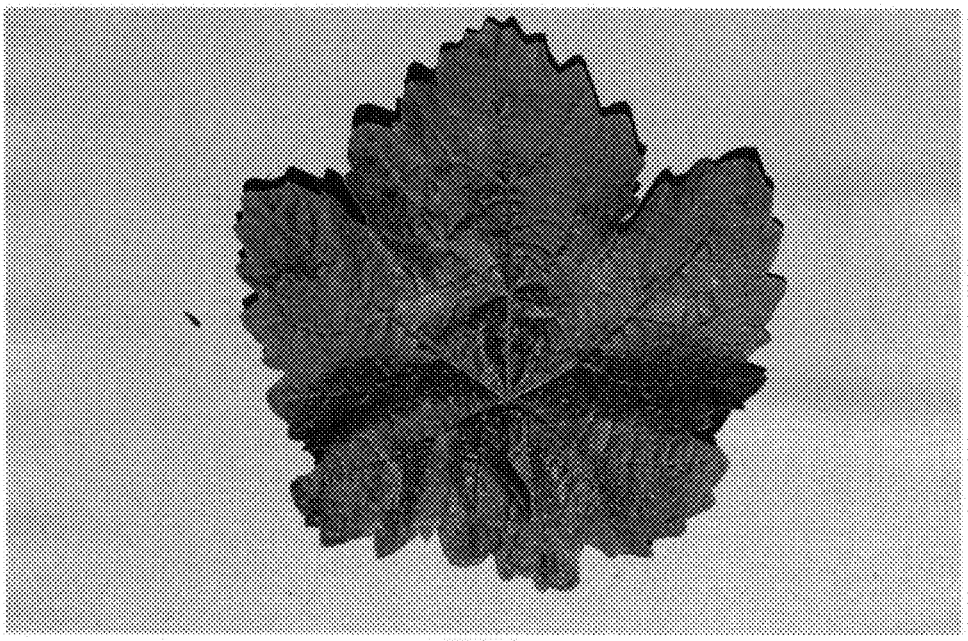
Figure 4:
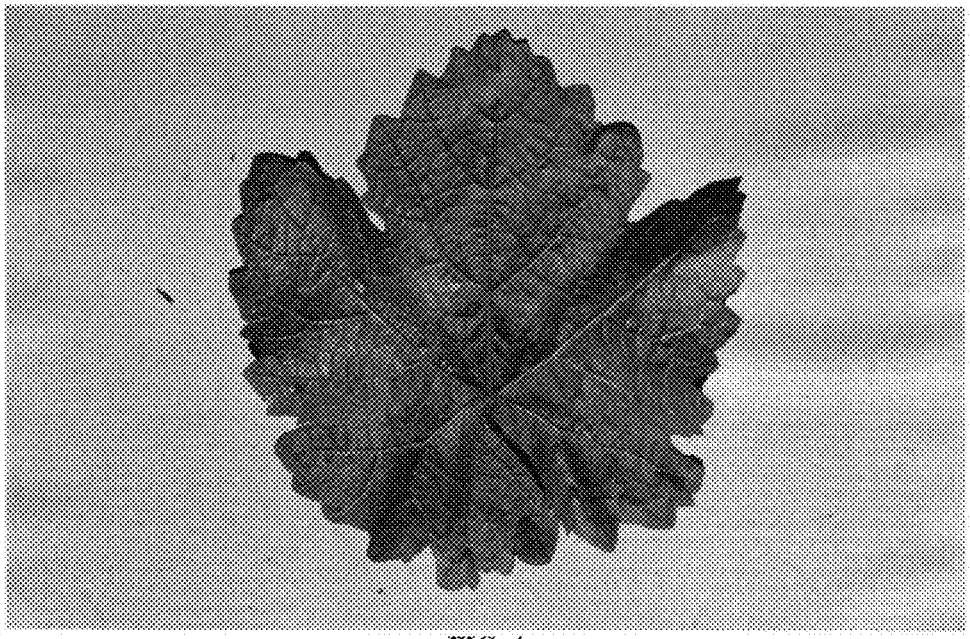
Figure 5:
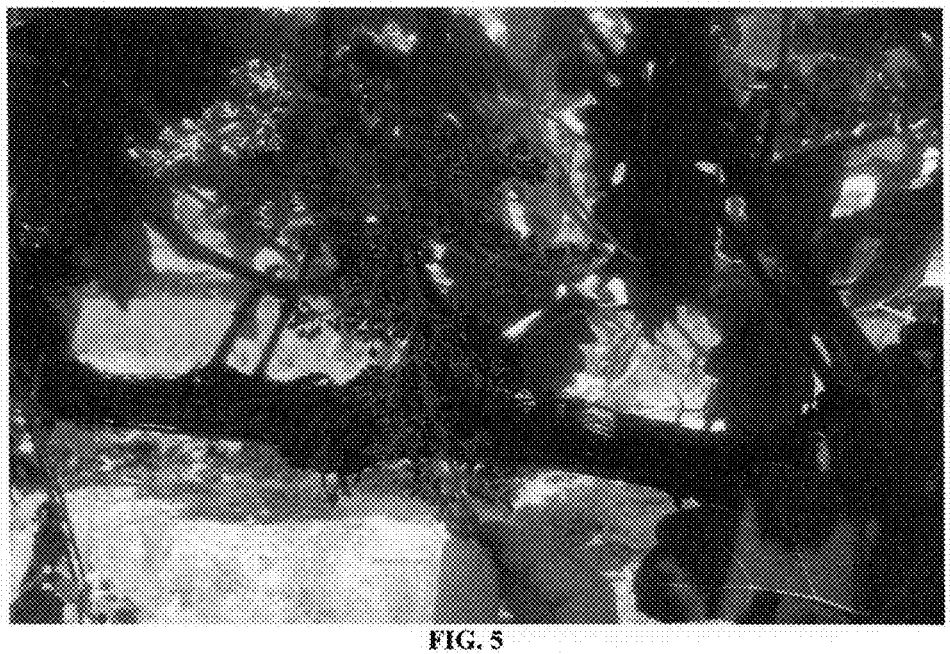
Figure 6:
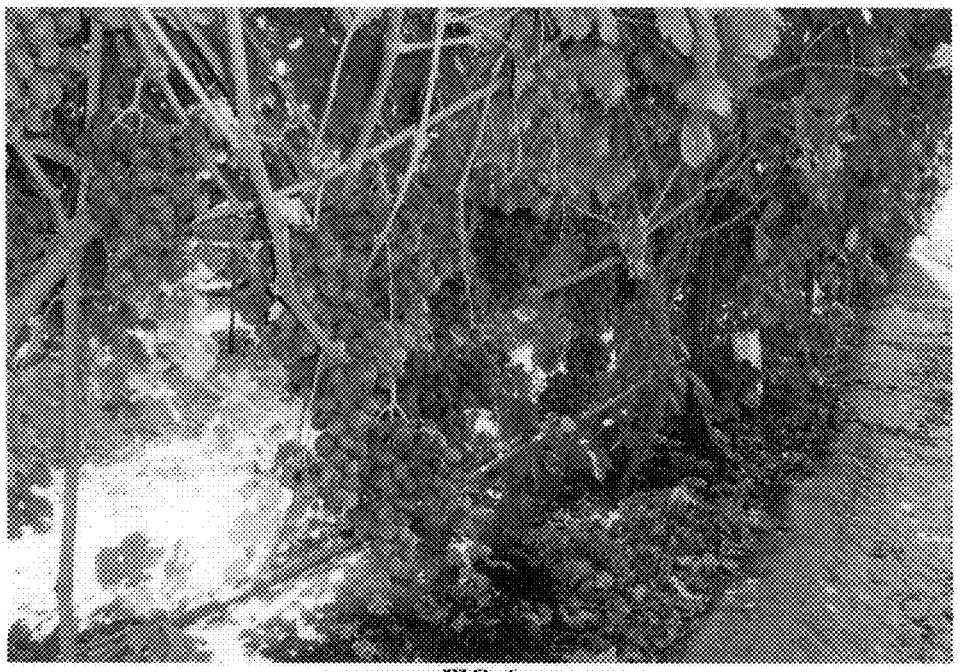
Figure 7:
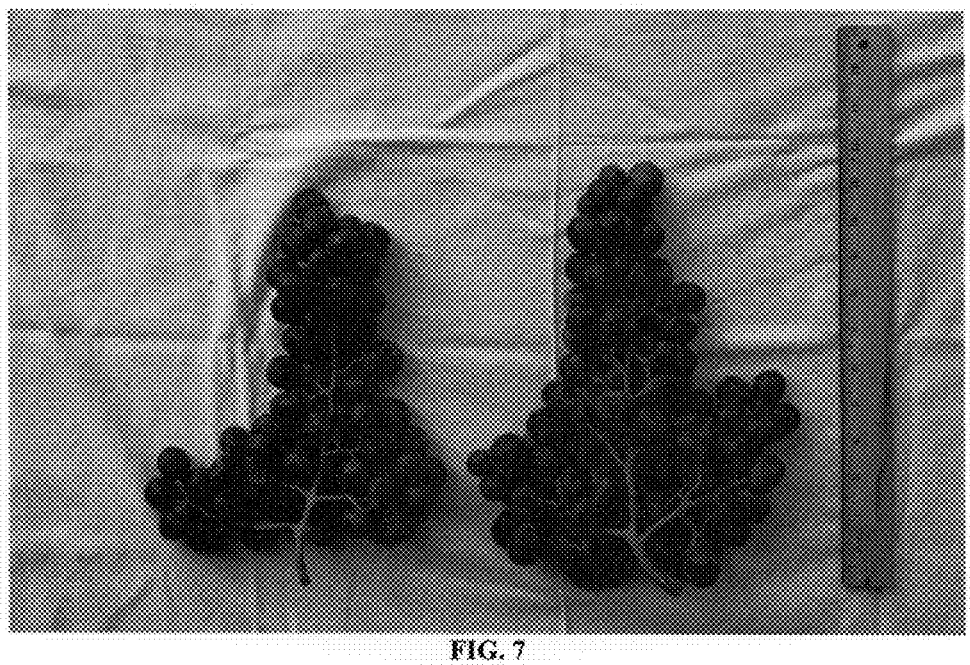
Figure 8:
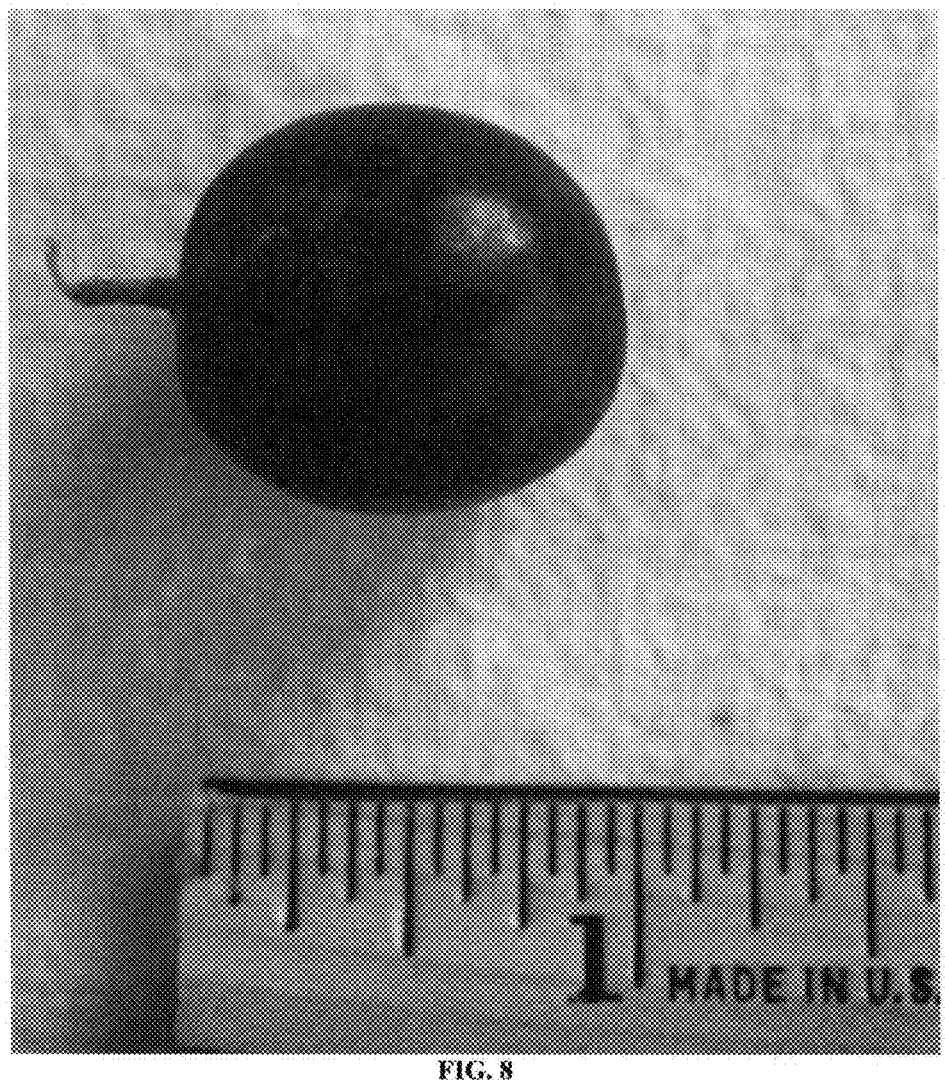

FIG. 1 shows overall vine and cane habit at bloom.
FIG. 2 shows a close up of a growing shoot tip at bloom.
FIG. 3 shows the upper surface of a mature leaf.
FIG. 4 shows the lower surface of a mature leaf.
FIG. 5 shows a close up of an immature primary fruit cluster.
FIG. 6 shows mature fruit clusters on the vine.
FIG. 7 shows mature primary fruit clusters at harvest.
FIG. 8 shows a close up of a single berry at harvest.

DESCRIPTION OF THE NEW VARIETY

The following detailed descriptions set forth the distinctive characteristics of 'CAR98-710'. The data which defines these characteristics were collected from asexual reproductions carried out in Delano, Calif. The plant history was taken on mature 7 year old grapevines grown under field conditions in Delano, Calif. All color references were obtained under natural light. Color references are primarily to the Munsell Color Charts for Plant Tissues by Munsell Color, 617 Little Britain Rd., New Windsor, N.Y. 12553-6148. Common color names are also occasionally employed.

DETAILED BOTANICAL DESCRIPTION OF THE NEW PLANT

Classification:
*Family.*—Vitaceae.
*Botanical name.*—*Vitis vinifera.*
*Variety name.*—'CAR98-710'.

Parentage:
*Female parent.*—'Black Globe' (U.S. Plant Pat. No. 17,875).
*Male parent.*—'552' (U.S. Plant Pat. No. 9,916).

Plant:

*Plant habit and growth.*—Trailing with light to moderate secondary shoot development.

*Time to maturity.*—3 to 4 years.

*Height* (*at maturity*).—Cordon: 120.0 cm. Canopy: 200.0 cm.

*Width* (*at maturity*).—190.0 cm.

*Vigor.*—High.

*Productivity.*—Medium.

Trunk:

*Diameter* (*measured* 60 *cm from floor*).—7.3 cm.

*Surface texture.*—Coarse, rough.

*Color.*—Exposed surface: 5YR 6/2. Non-exposed: 5YR 4/4.

Canes (dormant fruiting canes measured on April 3):

*Diameter* (*measured at base*).—1.55 cm.

*Length.*—112.0 cm.

*Surface texture* (*both immature and mature canes*).—Smooth.

*Form* (*woody shoot cross section form*).—Pith in center with diaphragm at nodes.

*Color* (*mature at base*).—5YR 4/6.

*Color* (*immature at* 6 *weeks*).—2.5GY 7/8. Anthocyanin: Absent.

*Internode length* (*upper mature sun cane*).—5.5 cm. Number of nodes: 40.

Time of bud burst (50% of buds broken): April 2.

Tendrils:

*Form.*—Bifid, and occasionally trifid.

*Size.*—General: Medium. Length (average): 16.0 cm to 22.0 cm on mature canes. Diameter (measured at base of tendril): 3.0 mm.

*Texture.*—Smooth, no pubescence.

*Distribution.*—Discontinuous. Predominate sequence: Tendril, tendril, no tendril, tendril, tendril, no tendril.

*Color* (*mature*).—Three weeks old: 5GY 6/6. Six weeks old: 2.5GY 8/6. Anthocyanin: Absent.

*Color* (*immature,* 1 *week old*).—2.5GY 7/8. Anthocyanin: Absent.

Growing tips (young shoot):

*Pubescence.*—Very slight.

*Color.*—2.5GY 6/6.

*Anthocyanin.*—2.5YR 5/8.

*Shape.*—Fully open.

*Apex.*—Normal, triangular.

Leaves:

*Shape.*—Pentagonal.

*Apex.*—Pointed.

*Base.*—Rounded.

*Margin.*—Irregular teeth.

*Height of teeth on margin.*—2.0 mm to 5.0 mm, variable.

*Shape of teeth on margin.*—Convex.

*Texture* (*mature leaf*).—Upper surface: Slight blistering. Lower surface: Glabrous.

*Immature leaf.*—Length: 6.5 cm at 2 weeks old. Width: 9.0 cm at 2 weeks old. Surface appearance: Shiny. Color: Upper surface: 2.5GY 7/10. Lower surface: 2.5GY 6/8.

*Mature leaf.*—Length: 10.0 cm at ninth node from growing tip. Surface appearance: Dull. Color: Upper surface: 5GY 4/4. Lower surface: 5GY 6/4.

*Venation.*—Pattern: Primary and secondary veins on the upper surface are visible due to their lighter color contrasting with the interveinal tissue; the lower surface veins are raised. Color: Upper surface: 2.5GY 8/6 (yellow-green). Lower surface: 2.5GY 8/4 (cream). Anthocyanin: Absent.

*Petiolar sinus.*—Mostly slightly open to slightly closed; upper leaf sinus slightly closed (90%) to slightly open (10%).

*Petiole.*—Length (on tenth leaf from tip): 7.0 cm. Diameter: 2.0 mm to 2.5 mm. Color: 2.5GY 8/8 (yellowish green) to 10R 5/8 (copper).

Floral cluster:

*General description and location.*—First floral cluster occurs on the fourth node.

*Quantity of inflorescences per cluster* (*average*).—300.

*Length* (*not including the peduncle*).—17.0 cm.

*Width.*—13.5 cm.

*Peduncle length.*—6.0 cm to 8.0 cm.

*Inflorescences.*—Hermaphroditic.

*Stamens.*—Upright.

*Anthers.*—Normal size, light yellow.

*Date of bloom.*—Beginning May 9$^{th}$, 50% by May 12$^{th}$ and 80% by May 13$^{th}$.

*Pollen amount.*—Moderate to abundant.

*Calyptra.*—Description: Complete separation from flower base. Color: 5GY 5/8.

Fruit:

*Time of year of commercial harvest and shipment.*—Mid August to late September.

*Cluster* (*primary bunches*).—General size: Large. Weight: 900.0 g. Length (without peduncle): 20.0 cm. Width: 16.0 cm. Density: Medium. Peduncle length: 5.5 cm. Peduncle diameter: 0.5 cm. Peduncle color: 2.5GY 6/6. Number of berries per cluster: Large cluster: 111. Medium cluster: 75. Small cluster: 37. Berry: Size: 9.0 g. Shape: Mostly globose. Uniformity: Very good. Brix content: 18.4 on August 21$^{st}$. Diameter: 2.3 cm. Length: 2.5 cm. Skin color: 5R 3/2. Pedicel: Length: 0.8 cm. Diameter: 0.2 cm. Color: 5GY 6/6. Strength of attachment to berry: Moderately strong.

*Cluster* (*secondary bunches*).—General size: Small. Weight: 90.0 g. Length (without peduncle): 6.4 cm. Width: 6.5 cm. Density: Medium. Peduncle length: 8.2 cm. Peduncle diameter: 0.23 cm. Peduncle color: 2.5GY 6/8. Number of berries per cluster: 11 berries. Berry: Size: Medium to large. Weight: 8.5 g. Shape: Mostly globose. Uniformity: High. Brix content: 17.6 on August 21$^{st}$. Diameter: 2.1 cm. Length: 2.6 cm. Skin color: 2.5R 4/6. Pedicel: Length: 1.0 cm. Diameter: 0.15 cm. Color: 5GY 7/8. Strength of attachment to berry: Strong.

Berry flesh:

*Color.*—Outer: 2.5GY 8/2. Inner: 2.5GY 8/5.

*Juice.*—Color: Clear. Production: Moderate.

*Thickness of skin.*—Medium.

*Flavor.*—Neutral.

*Fragrance.*—Absent.

*Texture.*—Medium.

Seeds: 1 to 2 prominent seed traces per berry.

*Length.*—0.4 cm to 6.0 cm.

*Color.*—Green to green-red.

*Firmness.*—Soft.

Disease and insect resistance: No particular resistance or susceptibility has been observed. Normal disease control practices can be used.

Winter hardiness and drought tolerance: Similar to commercial cultivars Autumn Royal and Summer Royal.

COMPARISON WITH PARENTAL AND COMMERCIAL VARIETIES

'CAR98-710' differs from the female parent grapevine plant named 'Black Globe' (U.S. Plant Pat. No. 17,875) in that 'CAR98-710' has seedless, globose shaped berries, whereas 'Black Globe' has seeded, obovate shaped berries.

'CAR98-710' differs from the male parent grapevine plant named '552' (U.S. Plant Pat. No. 9,916) in that 'CAR98-710' has black, globose shaped berries, whereas '552' has red, obovoid shaped berries.

'CAR98-710' differs from the commercial grapevine plant named 'Autumn Royal' (unpatented) in that 'CAR98-710' has medium to large fruit clusters and globose shaped berries maturing in September, whereas 'Autumn Royal' has large fruit clusters and ellipsoidal elongated berries maturing in October. Additionally, the fruit clusters of 'Autumn Royal' are generally more loosely filled, have less uniformity, and are longer than 'CAR98-710'.

'CAR98-710' differs from the commercial grapevine plant named 'Summer Royal' (unpatented) in that 'CAR98-710' is 4 to 5 weeks later maturing with larger berries weighing 9.0 grams, whereas 'Summer Royal' is early to mid season maturing with smaller berries weighing 5.0 grams. Additionally, 'CAR98-710' has berry clusters that maintain integrity into October, whereas 'Summer Royal' has berry clusters that shrivel (dry on the vine) beginning in late August.

I claim:

1. A new and distinct variety of grapevine plant named 'CAR98-710' as shown and described herein.

* * * * *